United States Patent [19]

Bianchini et al.

[11] Patent Number: 4,791,195

[45] Date of Patent: Dec. 13, 1988

[54] NOVEL OLIGOSACCHARIDES HAVING PHARMACOLOGICAL PROPERTIES BY DEPOLYMERIZATION OF HEPARIN

[75] Inventors: Pietro Bianchini; Giuseppe Mascellani, both of Corlo, Italy

[73] Assignee: Opocrin A.P.A., Corlo Modena, Italy

[21] Appl. No.: 921,332

[22] Filed: Oct. 21, 1986

Related U.S. Application Data

[63] Continuation-in-part of Ser. No. 582,933, Feb. 23, 1984, Pat. No. 4,629,699.

[30] Foreign Application Priority Data

Mar. 8, 1983 [IT] Italy ............................... 40021 A/83

[51] Int. Cl.[4] ...................... C08B 37/10; A61K 31/725
[52] U.S. Cl. ......................................... 536/21; 514/822
[58] Field of Search ..................... 536/21; 514/56, 822

[56] References Cited

U.S. PATENT DOCUMENTS

| | | | |
|---|---|---|---|
| 4,281,108 | 7/1981 | Fussi | 536/21 |
| 4,303,651 | 12/1981 | Lindahl et al. | 536/21 |
| 4,351,938 | 9/1982 | Barnett | 536/21 |
| 4,500,519 | 2/1985 | Lormeau et al. | 536/21 |

*Primary Examiner*—John Rollins
*Attorney, Agent, or Firm*—Bucknam and Archer

[57] ABSTRACT

Novel oligosaccharide fractions with valuable pharmacological properties are obtained from heparin. They have the same structural characteristics of heparin. The heparin fraction consists of oligosaccharides which contain end groups consisting of iduronic acid 2-sulfate, or glucosamine N, 6-disulfate. Further the oligosaccharides contain and monosaccharide endowed with reducing anomeric carbon, and are constituted by multiples of monosaccharide units.

5 Claims, 7 Drawing Sheets

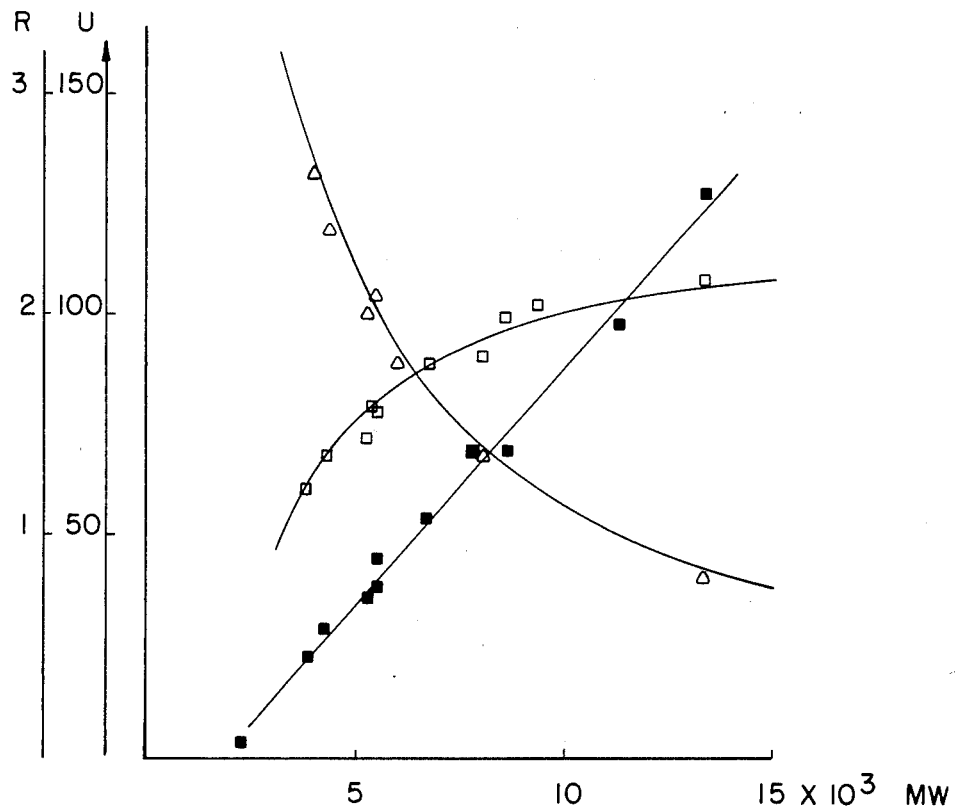
FIG.1 CHEMICALLY DEPOLYMERIZED HEPARIN. CORRELATION BETWEEN MOLECULAR WEIGHTS (MW) AND BIOLOGICAL ACTIVITIES.
- ■——■ U-APTT   Y=1.072 X-19.06  (r= 0.9967)
- □——□ U-AXa    $Y = 123.788 - \dfrac{2393.57}{X}$ (r=0.9826)
- △——△ R=U-AXa/U-APTT

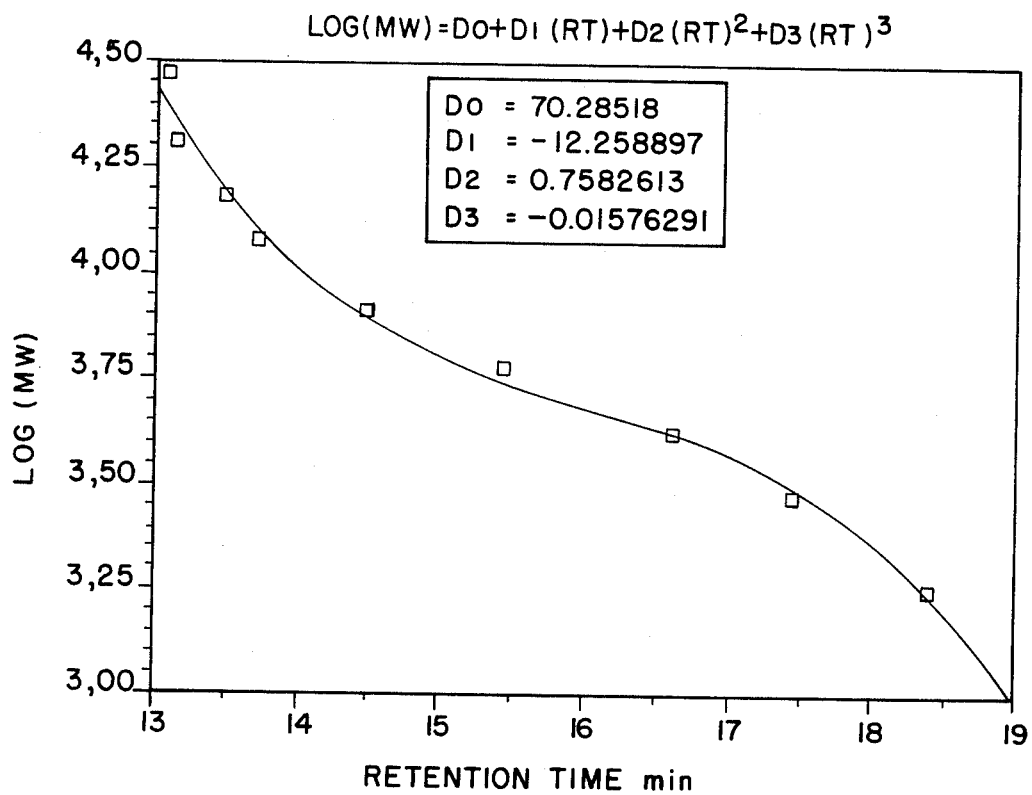

FIG. 2 GPC CALIBRATION CURVE OF HEPARIN MOLECULAR WEIGHT STANDARDS ON HPLC 125 AND 60 PROTEIN PAK COLUMN SERIE (WATERS). MOBILE PHASE 125 mM $Na_2SO_4$ AND 2 mM $Na_2HPO_4$ pH 6. FLOW 0.9 ml/min. DETECTOR REFRACTIVE INDEX. THE FUNCTION FITS WELL A THIRD ORDER POLINOMIAL EQUATION.

NUMBER OF STANDARDS: 9

| RT | MOL WT | LOG MW |
|---|---|---|
| 13.06 | 29,500 | 4.469 |
| 13.16 | 20,400 | 4.309 |
| 13.50 | 15,300 | 4.184 |
| 13.73 | 12,050 | 4.080 |
| 14.50 | 8,250 | 3.916 |
| 15.46 | 6000 | 3.778 |
| 16.63 | 4200 | 3.623 |
| 17.46 | 3000 | 3.477 |
| 18.40 | 1800 | 3.255 |

CALIBRATION COEFFICIENTS $D_0$  70.28518
$D_1$  -12.258897
$D_2$  0.7582613
$D_3$  -0.01576291

STD ERR OF ESTIMATE  0.0494577
CORR COEFFICIENT  0.99239

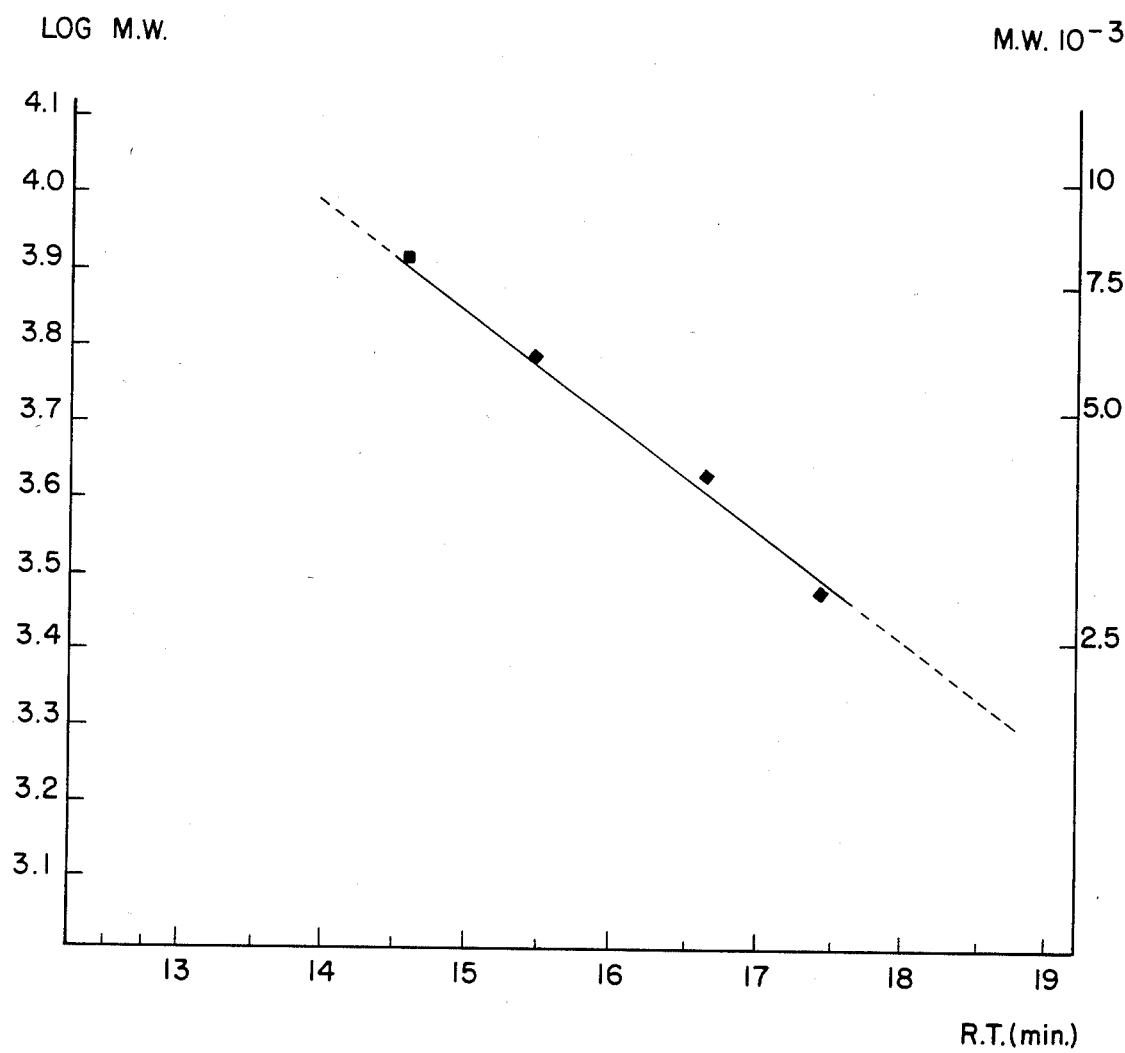
FIG. 2a MOLECULAR WEIGHT CALIBRATION CURVE.

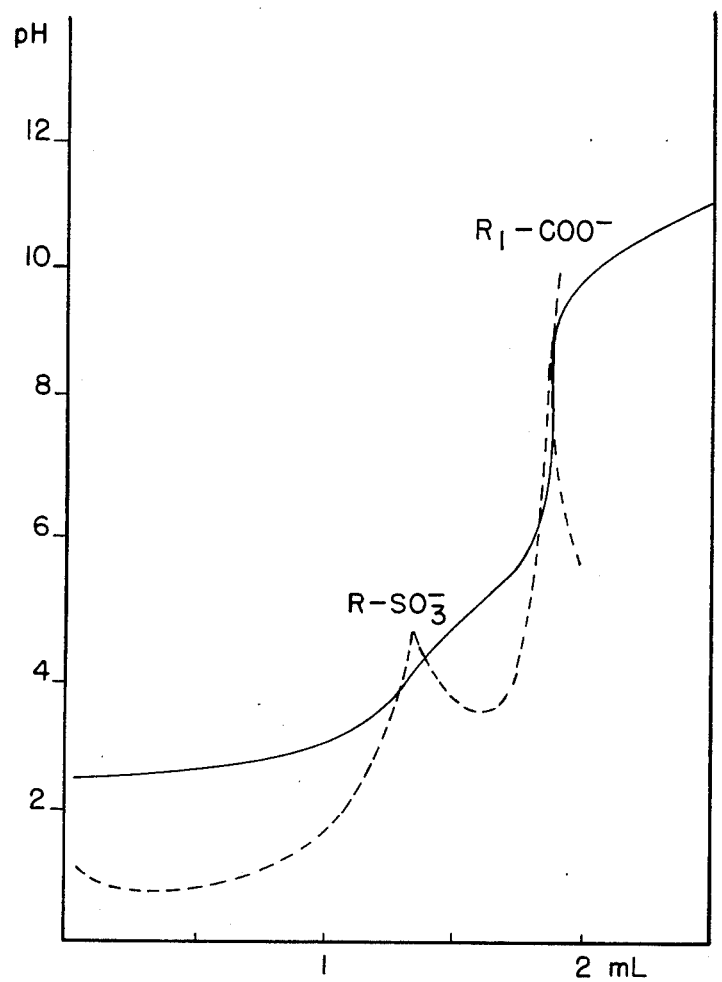
FIG. 3 EXAMPLE OF DIRECT (—) AND DIFFERENTIAL (---) POTENTIOMETRIC CURVE OF A DEPOLYMERIZED PRODUCT OP III.
(ACCORDING G. MASCELLANI et AL. IL FARMACO ED. PR. 43, 161, 1988).
$R_1 = 10.46$   $R_2 = 28.15$   $R_3 = SO_3^- / -COO^- = 2.227$

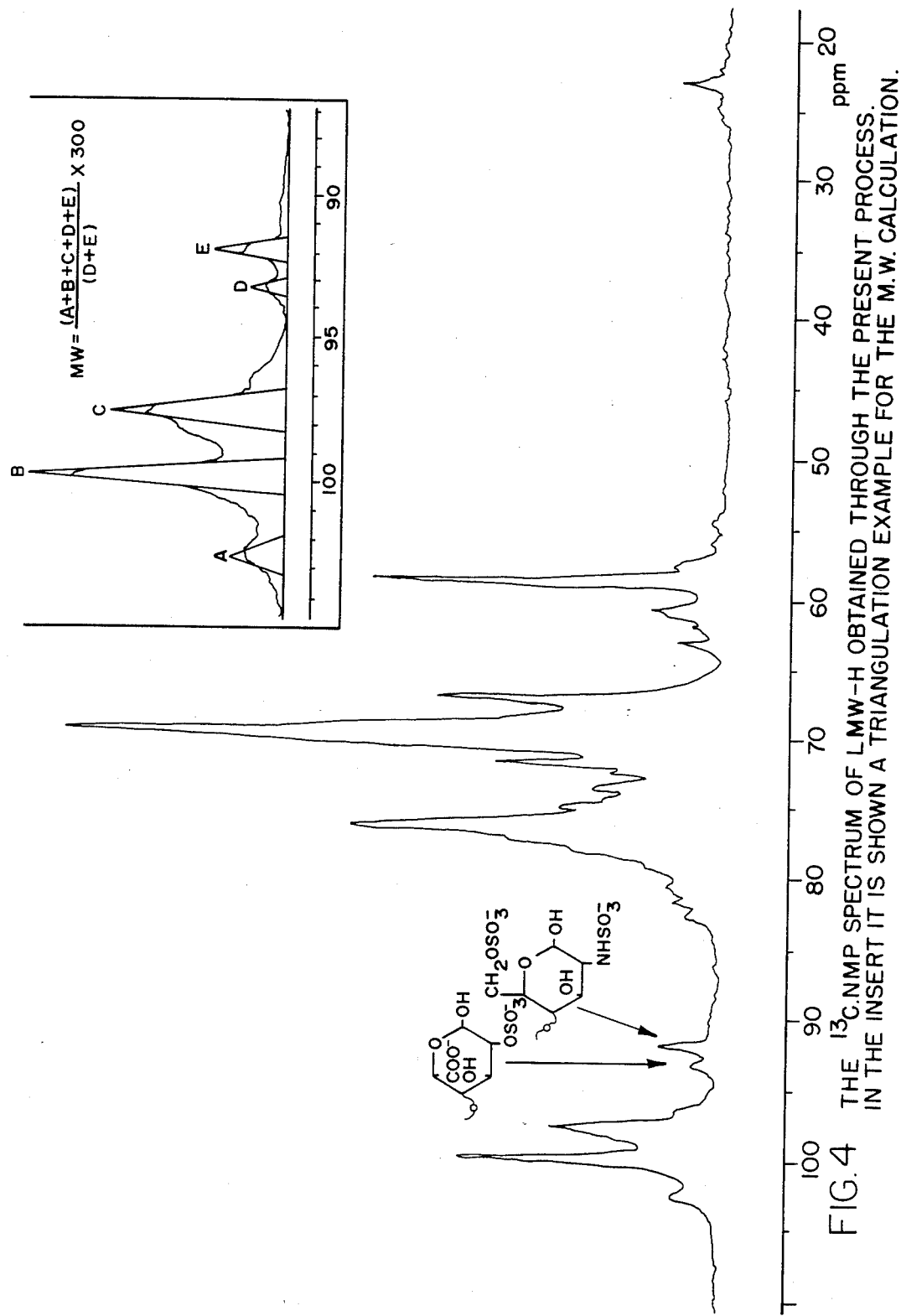
FIG. 4 THE $^{13}$C.NMP SPECTRUM OF LMW-H OBTAINED THROUGH THE PRESENT PROCESS. IN THE INSERT IT IS SHOWN A TRIANGULATION EXAMPLE FOR THE M.W. CALCULATION.

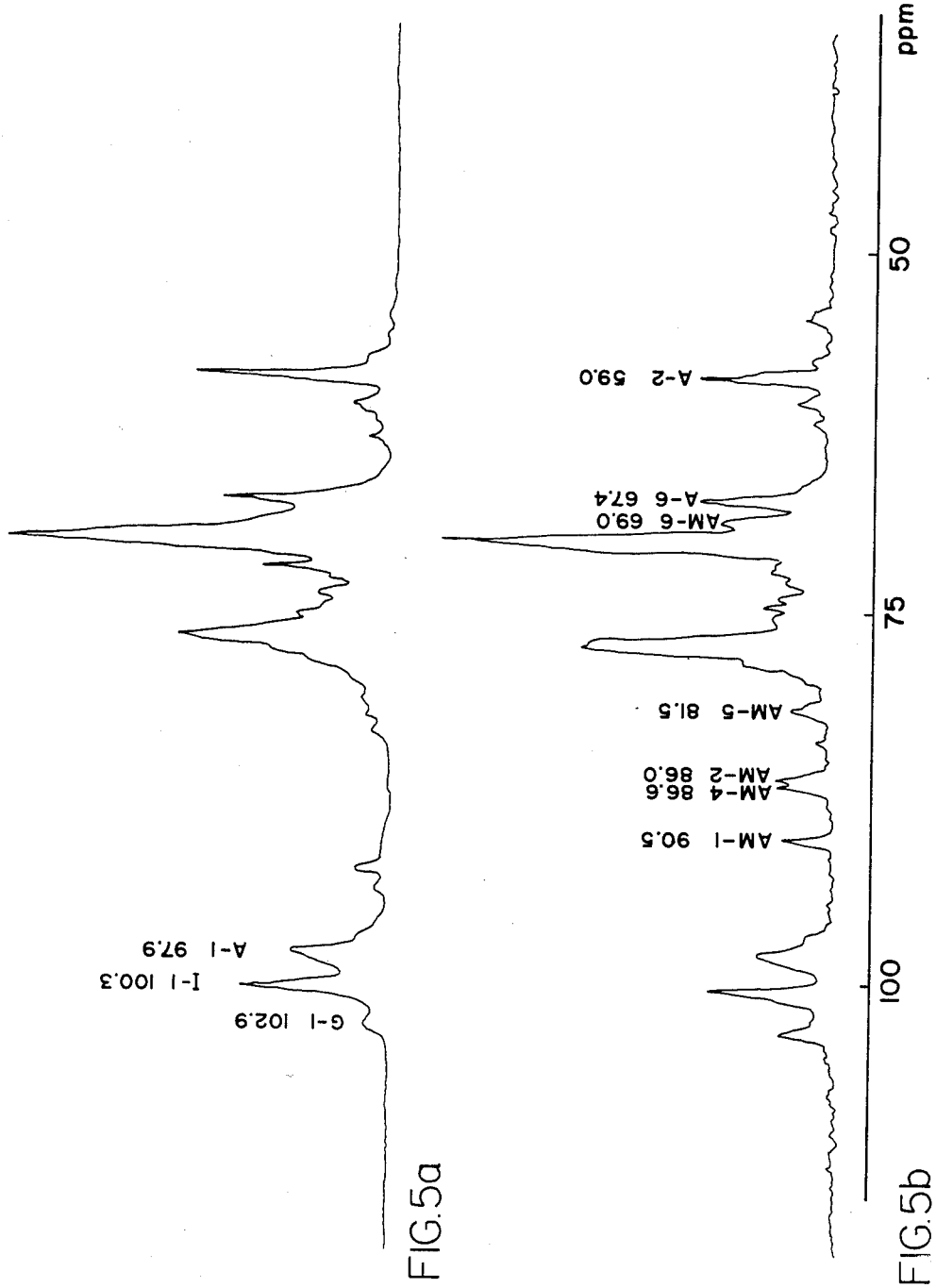

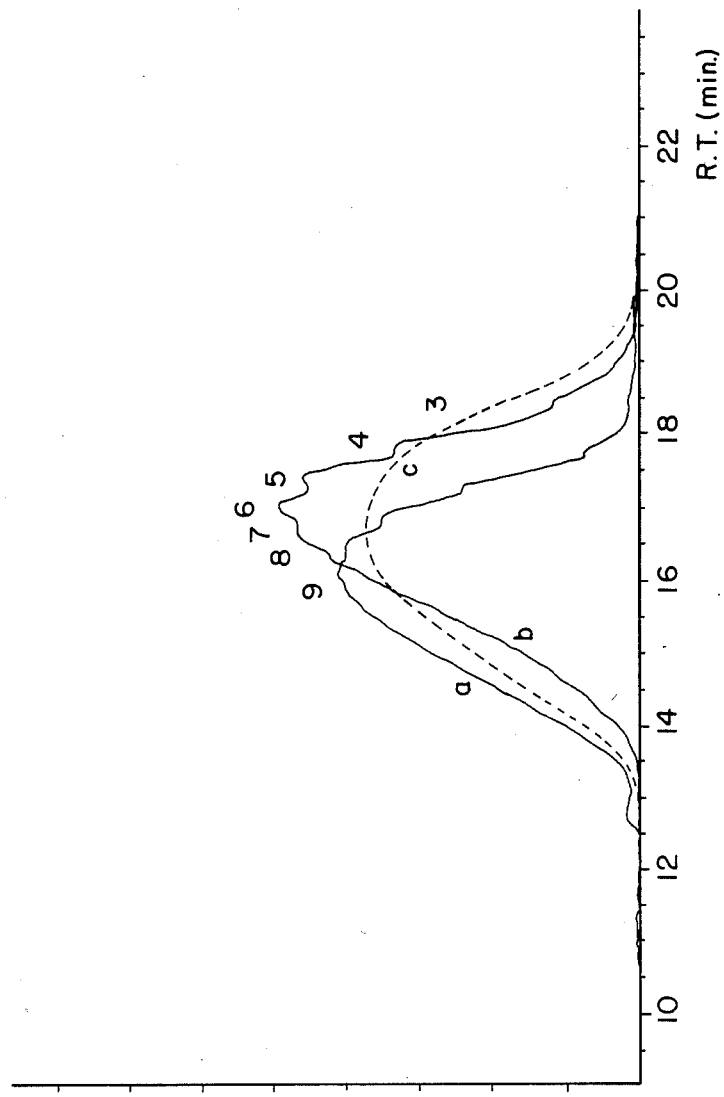

NOVEL OLIGOSACCHARIDES HAVING PHARMACOLOGICAL PROPERTIES BY DEPOLYMERIZATION OF HEPARIN

This application is a continuation-in-part of U.S. Ser. No. 582,933 filed Feb. 23, 1984, now U.S. Pat. No. 4,629,699.

The present invention relates to a novel chemical process for the preparation of low molecular weight oligosaccharide fractions from heparin. This invention also relates to the oligosaccharide fractions obtained by the process of this application, which exhibit valuable biological activities as shown by in vitro and in vivo tests.

It is known that individual oligosaccharides and oligosaccharide fractions which are composed of a mixture of oligosaccharides, derived from heparin, exhibit valuable antithrombotic activity associated with a relatively low anticoagulant activity as measured by global tests (APTT assay and pharmacopeial assay). However, the known processes for the depolymerization of heparin have given fractions of molecular weight lower than heparin but with structural characteristics different from the native heparin.

It has now been found, surprisingly, that the oligosaccharides and/or oligosaccharide fractions obtained by the process of this application maintain the structural integrity of native heparin. Further, the oligosaccharides and oligosaccharide fractions according to the present invention exhibit an antithrombotic activity which is not connected with AT III.

The oligosaccharides and/or oligosaccharide fractions obtained by the process of U.S. Ser. No. 582,933 have a relatively low mean molecular weight of approximately 5,000 Daltons. These oligosaccharides and/or oligosaccharide fractions are obtained from heparin by means of depolymerization processes, which are intended to produce fragments of molecular weight lower than those of the starting heparin. A few proposals have been made of processes, in which free radicals are involved, and which can lead to depolymerization of polysaccharides. It has now been found that the hydroxyl radical (HO.) is the most useful as initiator of depolymerization. It can be generated, for example by Fenton's reagent ($Fe^{++}$-$H_2O_2$), persulfate ion and systems based on oxygen, ascorbate and metal ions.

There has been developed, according to the application No. 582,933, a process of depolymerization of heparin based on generation of free radicals HO through divalent metal ions (such as $Cu^{++}$, hydrogen peroxide and ascorbic acid as described in Scheme 1) hereinbelow. The oligosaccharide fractions of the present invention are designated herein as OP-2123, OP-146, OP-111, OP-198, OP215P.

The natural mucosa-heparin used in the present process consists of the following dimers: L-iduronosyl-2-O-sulfate-N-sulfo-D-glucosamine 6-O sulfate ($I_S$-$A_{NS,\,6S}$) for 50% (m), L-iduronosyl-2-O-sulfate-N-sulfo-D-glucosamine ($I_S$-$A_{NS}$) for 30% (n), D-glucuronosyl-N-acetyl glucosamine (G-$A_{NA}$) for 10% (o) and D-glucuronosyl-N-sulfo-D-glucosamine (G-$A_{NS}$) for 10% (p). In some cases the iduronic 2-O sulfate acid ($I_S$) may have as "variant" the glucuronic acid (G). In the depolymerization process we have obtained the LMW H with a molecular weight of about 4500 D (corresponding to about 7,5 disaccharides). This low molecular weight heparin consists of the same disaccharides, whose statistical presence is: ($I_S$-$A_{NS,6S}$)≃3,5 (a); ($I_S$-$A_{NS}$)≃2,25 (b); (G-$A_{NA}$)≃0,75 (c); (G-$A_{NS}$)≃0,75 (d). Hereinbelow in the scheme are reported also the reducing end-groups.

Scheme 1
Structure of Native Heparin And Cleavage through the Free Radical Process
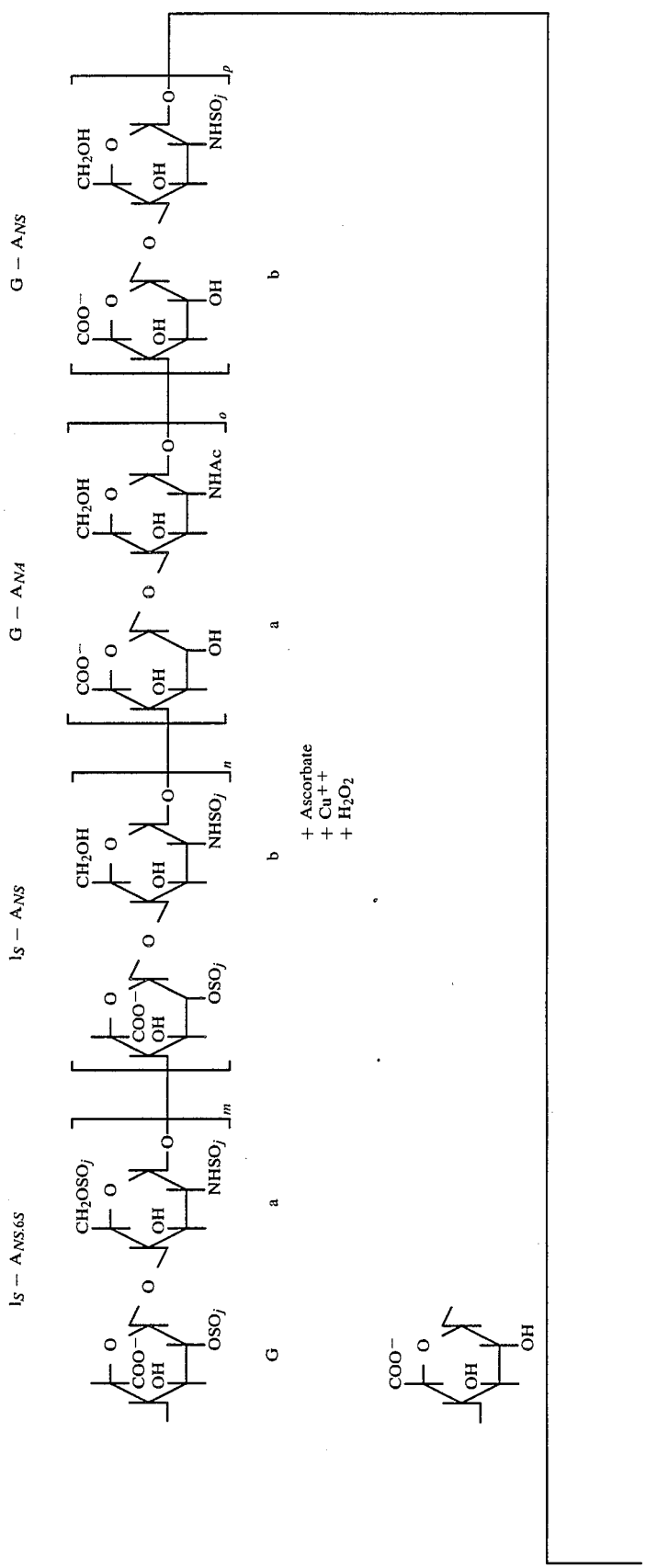

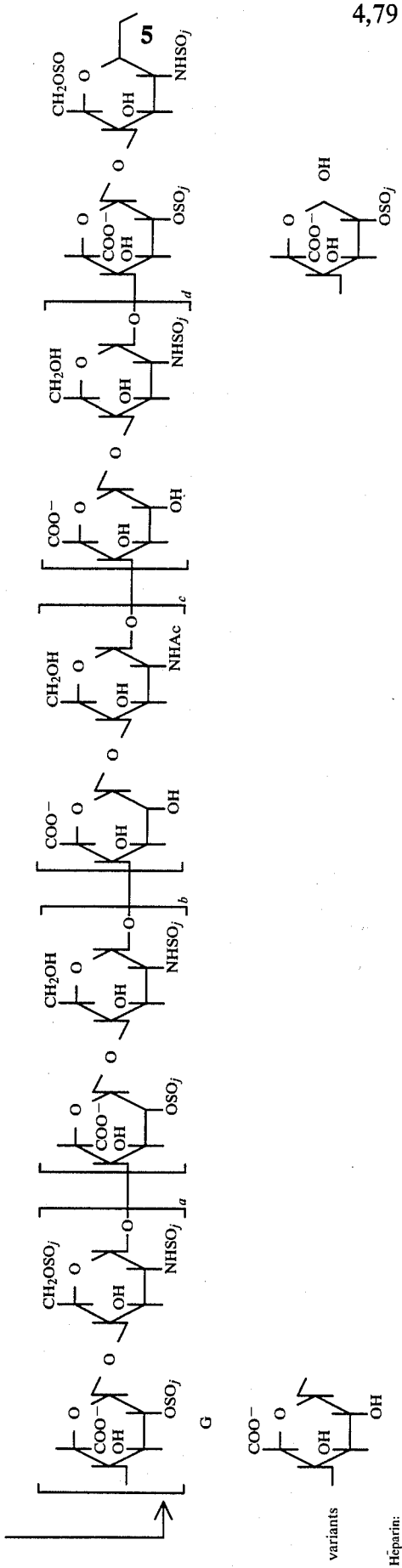

The invention is further illustrated by reference to the accompanying drawings of which:

FIG. 1 is a plot of the molecular weight and anticoagulant activity quantified in APTT units; AXA/units or AXa/APTT;

FIG. 2 is a calibration curve of heparin molecular weights utilizing the HPLC technique;

FIG. 2a is the same calibration curve of heparin molecular weights of FIG. 2 on a higher scale and showing a straight-line portion in a range of retention times";

FIG. 3 is a direct and differential potentiometric curve of the depolymerized product OP 111;

FIG. 4 shows the $^{13}$CNMR of the depolymerized heparin fractions according to the present invention;

FIGS. 5a and 5b illustrate the difference in $^{13}$CNMR spectrum of the heparin fraction according to the present invention and the heparin fraction obtained by the deaminative cleavage;

FIG. 6 illustrates the continuous progressive distribution of the heparin fraction according to the present invention.

The generation of HO. occurs in a 0.5–2% solution of heparin, with addition of a known amount of $H_2O_2$ in the presence of 0.001–0.02M cupric salt and at controlled pH and temperature as described in U.S. Ser. No. 582,933. Operative conditions described in the above-mentioned application, such as pH, temperature, hydrogen peroxide addition rate and reaction times, have been further investigated.

The depolymerized products obtained in the tests have been isolated, analyzed in various assays and characterized. It has been found that little or no depolymerization takes place in the range of pH 3–5. As the pH is raised above 6, the extent of depolymerization increases markedly.

Thus, the reaction is controlled by pH, temperature and reaction time. Free radical scavengers, such as catalase, could also be used for this purpose.

Different low molecular weight oligosaccharide fractions (LMW H), endowed with specific activities, have been obtained by carrying out the chemical depolymerization according to the process of U.S. Ser. No. 582,933.

The anticoagulant activity of these fractions, quantified in APTT units (activated partial thromboplastin time units) and the measure of the whole blood anticoagulant activity and their specific antiprotease (anti factor Xa and anti factor IIa) actions have been determined. Basu and co-workers, (New Eng. J. Med., 287, 324, (1972)). These studies have demonstrated that a linear relationship exists between molecular weight and APTT, while a hyperbolic relationship between the molecular weight of chemically depolymerized heparin-fractions and their anti-factor Xa activity (AXa-units) or AXa/APTT ratio has been observed as shown in FIG. 1. The anti Xa activity has been evaluated according to Teien A. N., Thrombosis Res., 8, 413, (1976).

The molecular weights have been calculated utilizing the HPLC technique in accordance with the calibration curve of FIG. 2.

The curve has been plotted using authentic samples of natural heparin fractions, which have been separated by gel filtration Chromatography on Sephacryl S-200 (Pharmacia), or Ultragel Ac.A. 202 and Ultragel Ac.A. 54 (LKB) columns.

The molecular weights of the fractions have been confirmed by electrophoresis on polyacrylamide using a standard method. [Hilborn J. C. and Anastassiadis P. A., Anal. Biachemistry, 39, 80 (1974)] and by a reference viscosimetric method [Johnson E. A. and Mulloy B., Carbohydrate Res., 51, 119, (1976)]. The molecular weight has also been evaluated on HPLC (Waters) by means of consecutive columns: Protein Pak 125 and Protein Pak 60 (Waters); Run conditions included eluent 0,125M $Na_2SO_4$ and 2 mM $Na_2HPO_4$ at pH 6; Flow rate 1,1 ml/min; Detector: UV and refractive index.

The calibration curve in the considered interval of this application is rectilinear as seen in FIG. 2a. The data show that under the experimental conditions of this application the obtained low molecular weight heparin OP-2123 obtained exhibited a molecular weight ranging between 4000 and 5000 Daltons.

In the overall depolymerization process no desulfation takes place, as shown by the test of total carboxyl and total sulfate groups and calculating the ratio $SO_3^{--}/COO^-$ prior to and after the depolymerization process, as shown in FIG. 3. This ratio was deduced through potentiometric analysis which was carried out on native heparin as well as on different intermediate fractions generated during the depolymerization process. The latter have been isolated during the process in the example that generated the fraction OP 111, an intermediate fraction as shown in Table III.

The products obtained by the process of the present invention have been subjected to the $^{13}$C.NMR spectroscopy to establish the structure. The sample was solubilized in $D_2O$. The $^{13}$C.NMR chemical shifts are given with respect to external reference, tetramethylsilane and using methanol as internal reference. The methanol chemical shift in $D_2O$ in comparison with that of tetramethylsilane was 51.75 ppm according to the procedure described by Casu B., Biochem. J., 197, 599, 1981).

The $^{13}$C.NMR spectra of the depolymerized heparin products, LMWH, remained essentially the same as the spectrum of the parent heparin, indicating retention of the native structure (See FIG. 5A).

In addition, the $^{13}$CNMR spectra of the typical depolymerized product exhibit two weak signals at 92,7 and 94,4 ppm due to reducing end groups of D-glucosamine-N-sulfate (alpha-anomer) and L-iduronic acid 2-sulfate respectively, as shown in FIG. 4. These signals distinguish the low molecular weight fractions from native heparin. These signals are one of the major distinguishing features of the depolymerization product represented by the batches OP-2123, OP 215 P, OP 146, OP 198, OP 111 obtained by a free radical depolymerization process as shown in FIG. 5A in contrast with other LMW H products which are obtained through deaminative cleavage, according to U.S. Pat. No. 4,500,519, for instance, in Example 1 of this patent. In the deaminative cleavage process peculiar signals indicating 2,5-anhydromannose residue (mostly 6-0 sulfate) are evident at 69.0 (am-6), 81,5 (am-5), 86.0 (am-2), 86,6 (am-4), 90,5 (am-1) ppm as shown in FIG. 5B.

The area of the two C-1 signals of the reducing residue of oligosaccharides obtained by the process of the present application, that is, signals at 92,7 and 94,4 ppm as related to the total area of anomeric carbons, that is, signals at 97,9 ppm (C-1 of glucosamine N-sulfate), 100,3 ppm, (C-1 of iduronic acid 2-sulfate), 102,9 ppm (C-1 of glucuronic acid corresponds to the number of monosaccharides contained in this particular depolymerized product, OP-2123, OP 215/P, OP 146, OP 111, OP 198.

Thus, assuming the monosaccharide average molecular weight is 300 Daltons, it it possible to calculate the average molecular weights of preparations according to the standard triangulation method as shown in the Insert of FIG. 4. These figures substantially correspond to values obtained by HPLC ($MW_n$) and polyacrylamide gel electrophoresis (P.A.A.) and are summarized in Table 1.

TABLE 1

MOLECULAR WEIGHTS OF DEPOLYMERIZED HEPARIN

| | SAMPLE DESIG- NATION | HPLC[a] $MW_n$ | $^{13}C.NMR$[b] | P.A.A.[c] |
|---|---|---|---|---|
| Example 3 | OP 119 | 1415 | 1700 | 1800 |
| Example 4 | OP 125 | 2100 | 2100 | 2300 |
| Example 5 | OP L51184 | 2880 | 2500 | 2800 |
| Example 6 | OP 220 | 3570 | 3650 | 3350 |
| Example 7 | OP 296/Ca | 3710 | 3300 | 3650 |
| Obtained under the same conditions as in Example 1 | OP 215/P | 4000 | 4400 | 3780 |
| | OP 146 | 4580 | 4470 | 4560 |
| | OP 111 | 4570 | 4100 | 4600 |
| | OP 198 | 5050 | — | 5460 |
| Example 8 | 311084 | 8000 | 7600 | 7200 |
| | 116–117 | 13500 | — | 13700* |

[a]High performance liquid chromatography
[b] $^{13}$CNMR spectroscopy
[c]Polyacrylamide gel electroplate
*Native heparin.

The gel permeation chromatographic (GPC) profile on HPLC and $^{13}C.NMR$ spectra indicate that the process catalyzed by free radicals leads to cleavage of glycosidic bonds of both uronic acids and 2-sulfamino-2-deoxy-D-glycopyranose in the heparin chains. On the contrary, the molecular weight distribution of the product LMWH obtained by nitrous acid cleavage according to U.S. Pat. No. 4,500,519, U.S. Pat. No. 4,351,938 exhibits 600 Daltons discontinuous ranges of molecular weights instead of the continuous progressive distribution of the product according the present application. These differences are clearly shown in FIG. 6. It should be noted that a continuous curve means periodicity and uniformity of structure.

In the product OP-2123 polydispersity (D) (i.e. the ratio of the weight average molecular weight ($MW_w$) to the number average molecular weight ($MW_n$) of the tested oligosaccharide varies between 1.18 and 1.35. Other depolymerized heparin fractions exhibit higher polydispersity, greater than 2.

Finally the operative parameters of the process described in application Ser. No. 582,933 (pH, reaction times and temperature) have been modified. We have obtained oligosaccharides, whose average molecular weight can vary as shown in Tab. 1, while at the operative conditions of Example 1 of this application we repeatedly obtained oligosaccharides with a molecular weight (HPLC $MW_n$) between 4000 and 5050 Daltons (OP 215/P; OP 146; OP 111; OP 198; OP 2123). The LMW H depolymerized fractions so obtained are a mixture of oligosaccharides and exhibit the following:

they contain an average 13–17 monosaccharide units.

The terminal groups of these oligosaccharides are unique and are composed of iduronic acid 2-sulfate or glucosamine-N, 6-disulfate. Both of these monosaccharides contain the reducing anomeric carbon which is not present in other depolymerized products obtained by nitrous acid deaminative cleavage described by other investigators.

They are constituted by multiples of "monosaccharide units", unlike the other products obtained through deaminative cleavage, (according to U.S. Pat. Nos. 4,303,651; 4,500,519; 4,351,938; 4,474,770; 4,401,662) which are found to be constituted of multiples of disaccharide units.

The oligosaccharides composing the low molecular weight heparin fractions according to the process of the present invention, contain even and odd numbers of saccharide units, while maintaining continuity while the other low molecular weight heparins obtained according to the cited patents have been constantly found to contain even numbers of saccharide units. It has also been found that the cleavage with $HNO_2$ acts only at level of glucosamine N-sulfate, while the free radical cleavage according to the present invention acts on glucosidic bonds of uronic acid as well as on 2-sulfamine-2-deoxy-D-glycopyranose.

The mixture of oligosaccharides obtained, with average molecular weight between 4000 and 5050 Daltons, maintains the absolute structural integrity of the native heparin as confirmed by the NMR spectrography charge density studies and more importantly from the ratio $SO_3^-/COO^-$ Based on various analytical results the chemical structure of the depolymerized product according to the present invention is presented in Scheme I. This product differs from the products of the other patents and in particular from the product of U.S. Pat. No. 4,303,651. As stated in this patent, in column 2, line 55–59, "reducing or unreducing terminal units may vary with type of method of preparation used, for example deaminative cleavage of heparin leads to the formation of 2,5 anhydro-D-mannose in reducing terminal position". The other alternative depolymerization process by periodate oxidation described in Example 2 of the same patent causes non-reducing end groups, since it splits the $C_2-C_3$ bonds of nonsulfated uronic acids, making glycosidic bonds of modified residues labile to alkali or when reduced, to acid, as shown by the earlier investigation of Casu B., "Structure and biological activity of heparin", Advance Carbohydr. Chem. Biochem., 43, 1985, Ac. Press, P. 51).

The low molecular weight heparin produced according to the process of the present application differs from the oligosaccharides of the U.S. Pat. No. 4,401,662 and of U.S. Pat. No. 4,474,770, since the product of these two patents comprise not more than 8 saccharide units, of which one is an N-sulfate-3-O-sulfate-D-glucosamine unit.

The low molecular weight heparin produced by the process of this application also differs from the product described in U.S. Pat. No. 4,500,519 because the latter:

is obtained by deaminative cleavage, contains terminal groups composed of 2,5-anhydro-D-mannitol, or 2,5-anhydro-D-mannose, or 2,5-anhydro-D-mannonic acid.

contains multiples of disaccharide units.

The low molecular weight heparin obtained by the process of this application also differs from the low molecular weight heparin of U.S. Pat. No. 4,351,938 because the latter also contains reducing end groups composed of 2,5 anhydromannose groups as stated in Column 14, line 28. Also it exhibits a polydispersity (D) of approximately 2,5 which is much higher than 1.34 which is the maximum dispersity of low molecular weight heparin fractions of the present invention. Further the product of U.S. Pat. No. 4,351,938 contains an even number of disaccharide units, contained in the mixture of oligosaccharides, which constitute the low molecular weight heparin.

U.S. Pat. No. 4,281,018 describes a low molecular weight heparin, which is obtained by N-desulfation through the intermediate heparamine, depolymerization, by heating in an acidic medium, with an oxidizing agent followed by sulfation. This process leads to a supersulfated low molecular weight heparin substantially different from that of the trisulfated disaccharide sequences, typical of natural heparin (Casu B., Nouv. Rev. Franc. Haematol., 26, 211, 1984).

In contrast with the work reported in the patents mentioned hereinabove, as starting heparin beef mucosa heparin has been used in the present work. This is similar to pig mucosa heparin and significantly different from beef lung heparin (Gatti G., Casu B., Perlin A. S., Macromolecules, 12, 101, 1979).

Mucosa heparin contains a high percentage of the so called "fast moving heparin" as determined by electrophoresis and a low percentage of the so called slow moving heparin (Bianchini P. and others, Arzneimittel., 35 (II), 251, (1985). The composition of this mucosa heparin is also shown by enzymatic digestion as described by Jaques L. B., Pharmacol. Rev., 31, 99, 1980) as is illustrated in Scheme I. The origin and the type of heparin utilized in this process are important because it is important to select the heparin exhibiting the best pharmacological properties. For example, the heparin induced thrombocytopenia phenomenon, frequently observed with beef lung heparin and with its fractions (Bell W. R., Ann. Intern. Med., 85, 155, 1976) is relatively uncommon with the low molecular weight heparin obtained from mucosa heparin.

The heparin of approximately 4500 molecular weight according to the process of this application exhibits valuable pharmaceutical properties and based on the extensive preclinical and pharmacologic data it exhibits antithrombotic activity with high efficacy, high safety and minimum side effects. This heparin fraction is referred to as OP-2123.

EXAMPLE 1

PREPARATION OF OLIGOSACCHARIDE FRACTIONS, SAMPLE OP-2123

Commercial beef mucosa heparin with an average molecular weight of 15,000 Daltons exhibiting 170 APTT/mg and 172 AXa/mg was subjected to depolymerization according to the process of U.S. Ser. No. 582,933. Ten grams of heparin was dissolved in 700 ml of an aqueous solution containing 30 grams (500 m.moles) of sodium chloride and 30 g (200 m.moles) of sodium acetate tri-hydrate ($CH_3COONa.3H_2O$). The pH was adjusted to 7.8 by means of 2N NaOH. The resulting solution was then added with constant stirring, first to 200 ml of an aqueous solution containing 3.5 g (20 m.moles) of ascorbic acid, adjusted to a pH 7-7.5 by means of 2N NaOH, and then added to 200 ml of an aqueous solution containing 0.45 g (2.25 m.moles) of cupric acetate monohydrate. Subsequently 15 ml of 36% hydrogen peroxide (180 m.moles) were added very slowly under stirring. The pH was continuously adjusted to 7.8 by means of 2N NaOH and the mixture was kept at 50° C. for 20 hours.

After concentration under vacuo to one-half the volume, an amount of 3% by weight, referred to the volume of the mixture, of EDTA sodium salt was added, thepH was adjusted to 6.5-7 and the product was precipitated by addition of two volumes of methanol. The product was purified by repeating twice the precipitation with methanol. This product is designated herein as OP-2123.

The yield by weight of the low molecular weight heparin product composed of oligosaccharides having an average molecular weight of 4500 Daltons was 81%. The biological characteristics of this product are shown in Table II.

In the experimental thrombosis test, when OP 2123 is administered intravenously, it exhibits antithrombotic activity in rats in the proportion of 100 arbitrary units in comparison with 136 units of native heparin.

In the bioavailability studies, when 3.125 mg/kg of native heparin and of low molecular weight fraction OP-2123 are administered subcutaneously to rats, plasma levels expressed as area under curve of anti-Xa activity of 378 and 1161 respectively are obtained. These results clearly show that the low molecular weight heparin OP-2123 is three times more bioavailable than native heparin in terms of the anti Xa activity. On the contrary, when OP-2123 is administered by the endo-ileal route, the bioavailability is eight times higher than heparin.

TABLE II

| | | | | | BIOAVAILABILITY OF AXa ACTIONS* AUC** | | |
|---|---|---|---|---|---|---|---|
| | APTT (U/mg) | AXa (U/mg) | MW | eq —$SO_3H$ eq —COOH | IV | SC*** | E IL**** |
| Heparin | 170 | 172 | 15000 | 2.38 | 136 | 378 | 411 |
| LMW Heparin | 30 | 78 | 4500 | 2.35 | 100 | 1161 | 3317 |

*According to Reyers S. and others, Thromb. Res., 18, 699, 1980.
**Area under curve (AUC).
***After administration of 3.125 mg/kg in rats by subcutaneous (SC) route (expressed as anti-Xa activities).
****After administration of 22 mg/kg in rats by endo-ileal (E IL) route (expressed as anti-Xa activity).

EXAMPLE 2

STUDIES ON THE RATE OF DEPOLYMERIZATION

One hundred grams of commercial beef mucosa heparin, molecular weight 13400, has been depolymerized according to the procedure of Example 1. From the reaction mass during the addition of hydrogen peroxide, samples have been taken periodically and an intermediate reaction product has also been isolated. Molecular weight (HPLC) and potentiometric curves have been determined. The values obtained hereinbelow have been obtained.

TABLE III

| | Hrs. | M.W. | S % | Uronic Acids | $SO_3$—/COO— |
|---|---|---|---|---|---|
| Starting material | 0 | 13400 | 10.37 | 28.16 | 2.23 |
| Intermediate | 1 | 8100 | 10.46 | 28.15 | 2.25 |

TABLE III-continued

| | Hrs. | M.W. | S % | Uronic Acids | SO₃—/COO— |
|---|---|---|---|---|---|
| product OP 111 | 2 | 4570 | 10.44 | 28.10 | 2.23 |

The final product OP 111 in a yield of 76.3% is obtained after 2 hours.

The data show that in spite of significant reduction in molecular weight, the intermediate products exhibits the same sulfate, uronic and $SO_3^-/COO^-$ ratio.

EXAMPLE 3

EXHAUSTIVE DEPOLYMERIZATION STUDIES

Twenty five grams of heparin, previously depolymerized by the process of Example 1, having the following characteristics: (APTT u/mg=28; U-AXa/mg=83, in vivo antithrombotic activity 116, molecular weight 4300) was subjected to a process of further depolymerization, as described in the following.

25 grams of the low molecular weight fraction was poured into 200 ml of water with 0.75 of copper acetate and 8.75 g of sodium ascorbate. Then 180 ml of 16% hydrogen peroxide was slowly added under stirring during a period of two hours at 65°-70° C. The pH was kept at 7.4, by means of NaOH. The resulting solution, allowed to settle overnight, cooled at room temperature, adjusted to pH 6, was transferred on a chelex 100 ® column (2.8 φ×13 cm), then on an amberlite ® column (IRA. 400 OH- form, 4.2 φ×8 cm) and subsequently on a polystyrene column, strongly acid in the H+ form.

The eluate was adjusted with NaOH to pH 7, and freeze-dried. The product 19.55 g (78% yield) was a low molecular weight heparin designated as OP 119. Its characteristics, compared with the starting product, are reported in Table IV.

TABLE IV

| Product | M.W. | S % | Uronic Acids % | eq⁻SO₃H / eq⁻COOH |
|---|---|---|---|---|
| LMW OP 119 | 4300 1700 | 10.78 | 31.23 | 2.09 2.12 |

In spite of the reduction in molecular weight, the ratio $SO_3H/COOH$ is the same as in the OP-2123 sample.

PREPARATION OF DEPOLYMERIZED HEPARIN UNDER DIFFERENT EXPERIMENTAL CONDITIONS

In Example 4, the material was obtained under the same conditions of Example 3, but at a temperature of 60° C. In Example 5, the pH was 7.3 and the temperature was 55° C. In Examples 6 and 7, the temperature and pH were as in Example 2 but at hydrogen peroxide addition times of 3.5 and 3.0 hours respectively. The material of Example 8 was prepared under the same conditions as in Example 1, but at pH 6.5 and at 30° C.

BIOLOGICAL COMPARISON—AFFINITY FOR ANTITHROMBIN III

U.S. Pat. No. 4,303,651 by Lindal et al. claims fragments of heparin having 14-18 sugar units, obtained through various depolymerization processes, mainly characterized by high affinity for antithrombin III. All the depolymerized products were characterized and subfractionated by affinity chromatography as stated in Example 1, column 3, line 18; Example 2, column 4, line 14. In U.S. Pat. No. 4,401,662 and U.S. Pat. No. 4,474,770, after the depolymerization process, which is mainly based on deamination with nitrous acid, further purification on AT-III affinity chromatography is described, and it is stated that the resulting product has high affinity for antithrombin III. The high AT-III affinity is not a significant sole factor for in vivo antithrombotic activity.

On the contrary, as it is evident from the data reported below, the product according to this application OP-2123 exhibits low affinity for antithrombin III (AT-III) as demonstrated by strong antithrombotic action in rats in which antithrombin III was inhibited by specific antibodies to AT-III. The antithrombotic activity of OP 2123 is therefore based on a mechanism different from that of the above mentioned patents, in which it is stated that the products mediate their antithrombotic actions through AT-III. A pattern of experimental thrombosis was used according to Reyers et al., Thromb. Res., 18, 699 1980) carried out on normal rats and on rats in which AT-III had been blocked through administration of antithrombin antibodies (AB rats). The results are shown in Table V and V1.

TABLE V

| COMPARATIVE ANTITHROMBOTIC ACTIONS OF OP 2123 IN NORMAL AND AT-III DEPOLYMERIZED RATS | |
|---|---|
| | Thrombi weight |
| Thrombi in normal rats | 1.84 + 0.31 |
| Thrombi in AT-III - Ab rats | 4.82 + 0.58 |
| Thrombi in AT-III - Ab + LMW OP 2123* rats | 0.78 + 0.35 |

*0.5 mg/Kg of low molecular weight heparin OP 2123 in single dose. The test was carried out in 10 animals per group.

Thrombosis resulted much more evident in rats in which antithrombin had been blocked with anti-antithrombin III antibodies. The data show that the antithrombotic activity of OP 2123 is due to a mechanism other than through AT-III and that OP-2123 exhibits low affinity for antithrombin III (AT III).

TABLE VI

COMPARATIVE STUDIES ON THE ANTITHROMBOTIC ACTIONS OF VARIOUS LOW MOLECULAR WEIGHT FRACTIONS IN CONTROL AND AT-III DEPLETED (ANTIBODIES) RATS

| | U-AXa* | Antithrombotic activity $ED_{50}$ (mg/Kg) | |
|---|---|---|---|
| | | | with Ab AT III** |
| LMW according U.S. Pat. No. 4,500,519 | 140.5 | 0.25 + 0.036 | 0.37 + 0.07 |
| LMW OP 2123 according to the present application | 78 | 0.14 + 0.028 | 0.21 + 0.04 |
| LMW according U.S. Pat. No. 4,303,651 | 181.4 | 0.23 + 0.034 | 0.29 + 0.04 |

*chromogenic method
**Ab-AT III

The data in Table VI show that LMW H OP-2123 exhibits lower anti Xa but higher antithrombotic activity than the products of U.S. Pat. No. 4,500,519 and U.S. Pat. No. 4,303,651.

What is claimed is:

1. A heparin fraction which is a mixture of oligosaccharides containing an average of 13–17 monosaccharides, said oligosaccharides containing end groups composed of iduronic acid 2-sulfate, or glucosamine N, 6-disulfate, said end-groups monosaccharides containing the reducing anomeric carbon, said oligosaccharides being constituted by multiples of monosaccharide units and having a 4000–5000 molecular weight.

2. The heparin fraction according to claim 1 wherein the polydispersity is 1.18–1.35.

3. The heparin fraction according to claim 1 wherein the $SO_3^-/COO^-$ ratio is essentially the same as in heparin.

4. A heparin fraction according to claim 1 which exhibits $^{13}CNMR$ signals at 92.7; 94.4; 97.9; 100.3; 102.9.

5. A heparin fraction which exhibits a progressive distribution and which contains even and odd number of saccharide units.

* * * * *